United States Patent [19]
Ozaki et al.

[11] Patent Number: 4,507,245
[45] Date of Patent: Mar. 26, 1985

[54] PROCESS FOR THE PRODUCTION OF A RARE EARTH METAL ALKOXIDE

[75] Inventors: Yoshiharu Ozaki, Musashino; Kimiyoshi Kaneko, Isehara; Senshu Mitachi, Atsugi, all of Japan

[73] Assignee: Hokko Chemical Industry Co., Ltd., Tokyo, Japan

[21] Appl. No.: 509,017

[22] Filed: Jun. 29, 1983

[30] Foreign Application Priority Data

Jun. 6, 1982 [JP] Japan ............................ 57-1162468
Apr. 7, 1983 [JP] Japan ............................ 58-59978

[51] Int. Cl.$^3$ ........................ C07C 29/68; C07C 31/28
[52] U.S. Cl. .......................... 260/429.2; 156/DIG. 63
[58] Field of Search .................. 260/429.2, 429.1; 156/DIG. 63

[56] References Cited

U.S. PATENT DOCUMENTS

| | | | |
|---|---|---|---|
| 3,278,571 | 10/1966 | Khodabakhsh et al. | 260/429.2 |
| 3,420,861 | 1/1969 | Ropp et al. | 260/429.2 |
| 3,518,287 | 6/1970 | Rinse | 260/429.2 |
| 3,634,476 | 1/1972 | Rinse | 260/429.2 |
| 3,635,658 | 1/1972 | Ferri et al. | 260/429.2 |
| 4,003,937 | 1/1977 | Garibaldi et al. | 260/429.2 |
| 4,119,554 | 10/1978 | Fujiwara | 501/135 |

FOREIGN PATENT DOCUMENTS 3324377 1/1984 Fed. Rep. of Germany .

OTHER PUBLICATIONS

Zeitschrift Anorganische und Allgemeine Chemie, vol. 325 (12), pp. 67–71 (1963).
Inorganic Chemistry, vol. 5 (3), pp. 342–346 (1966).
Bradley, D. C., Advance Inorg. Chem. Radiochem., vol. 15, pp. 259–322 (1972).
Mehrotra, R. C. et al., Inorganic Chim. Acta, Rev., vol. 5, pp. 127–136 (1971).
Kirshenbaum, K. S. et al., Nouveau Journal Chimie, vol. 7 (12), pp. 699–701 (1983).
Namy, J. L. et al., J. Organic Chemistry, vol. 49 (11), pp. 2045–2049 (1984).
Singh, M. et al., J. Indian Chemical Society, vol. 55 (7), pp. 643–644 (1978).
Agarwal, S. K. et al., Z. Naturforsch, Teil B., pp. 50–54 30B (1-2)(1975).

Primary Examiner—Ben R. Padgett
Assistant Examiner—M. Moskowitz
Attorney, Agent, or Firm—Larson & Taylor

[57] ABSTRACT

A new improved process of producing a rare earth metal alkoxide is now provided, which comprises reacting a rare earth metal carboxylate with an alkali metal alkoxide in an inert organic solvent under anhydrous conditions, and which can be conducted in a facile way and give the desired rare earth metal alkoxide of a high purity in a high yield.

10 Claims, No Drawings

PROCESS FOR THE PRODUCTION OF A RARE EARTH METAL ALKOXIDE

SUMMARY OF THE INVENTION

This invention relates to a process of producing an alkoxide of a rare earth metal which is useful as a starting material for the production of a rare earth metal oxide. The rare earth metal oxides are, in turn, useful, for example, as additives for improving the properties of various ceramic products.

BACKGROUND OF THE INVENTION

In the recent years, the electronics industry has gained a great advance, and concurrently various kinds of rare earth elements have became utilized in a wide variety of applications. Particularly, in the field of "Fine Ceramics" industry, various kinds of the oxides of rare earth metals have overtaken some important roles. Especially, yttrium oxide is now calling great attentions, because the yttrium oxide can be admixed with zirconia (i.e., zirconium oxide) for the purpose of controlling the phase-transition of zirconia ceramic products. In these years, it has been found that the method of producing the oxides of rare earth metals, including the yttrium oxide, can be carried out by hydrolysis of such an alkoxide of a rare earth metal represented by the following general formula $$M(OR)_3 \qquad (I)$$

wherein M denotes a rare earth metal element such as scandium, yttrium, lanthanum, cerium, praseodymium, neodymium, samarium, europium, gadolinium, terbium, dysprosium, holmium, erbium, thulium, ytterbium and lutecium; and R denotes an alkyl group, preferably an alkyl group containing 1 to 10 carbon atoms.

In the prior art, different processes of preparing the rare earth metal alkoxide of the general formula (I) which is useful as the intermediate materials for use in the production of the rare earth metal oxides are known, including the under-mentioned processes:

(1) A first process comprising reacting anhydrous scandium chloride with dry methanol (see the "Zeitschrift Anorganische und Allgemeine Chemie" 325 (1-2) pages 67-71, (1963)).

(2) A second process comprising reacting an anhydrous rare earth metal chloride with an alkali metal alkoxide in an inert, dry organic solvent (see the "Proceeding Nucleus Radiation Chemical Symposium" pages 15-19 (1964); the "Chemistry and Industry" page 120 (1963); ditto, Vol. 9, pages 382-383 (1965); ditto, Vol. 32, pages 1379 (1966); the "Chemische Berichte" Vol. 93, pages 652-657 (1960); the "Inorganic Chemistry" Vol. 5(3), pages 342-346 (1966); and U.S. Pat. No. 3278571 specification, and (3) A third process comprising reacting a rare metal element with an alkanol in the presence of mercuric chloride as catalyst (see the "Inorganic Chemistry" Vol. 5(3), pages 342-346 (1966); and U.S. Pat. No. 3278571 spec.).

With all the above-mentioned processes of the prior art, however, these processes suffer from such disadvantages that the desired rare earth metal alkoxides can be obtained only in a poor yield and also contain some quantities of detrimental impurities. Consequently, the rare earth metal oxide products as obtained from such rare earth metal alkoxides of a low purity are also containing considerable quantities of the impurities. It follows that some operations of the purification are required in order to yield such a rare earth metal alkoxide product of a high purity which can provide a high purity grade of the rare earth metal oxide products. In the consequence, the cost for the production of the rare earth metal alkoxide of a high purity is inevitably expensive, rendering the resultant rare earth metal oxide products expensive, too. The first and second processes of the prior art essentially require the starting rare earth metal chloride employed should be anhydrous, as otherwise the desired reaction substantially cannot proceed. Besides, amongst the above-mentioned processes of the prior art, the first and second processes of the prior art are particularly disadvantageous in that the anhydrous rare earth metal chlorides employed as the starting material are normally of a very much highly hygroscopic property and are very difficult to be handled in a large quantity in commercial practice. The above-mentioned second process of the prior art is also disadvantageous in that the rare earth metal elements employed as the starting material are normally very expensive and the necessary reaction cannot be finished without conducting the refluxing of the reaction mixture under heating for a long period of time, so that this process is very time-consuming and is not suitable as a commercial method which is to be carried out in a large scale. Furthermore, all the first, second and third processes of the prior art as mentioned above involve the use of the chlorides as the starting material or as the reaction reagent or as the necessary catalyst, and usually a non-neglectable quantity of the chloride anion should necessarily be migrated into the intermediate products and even into the final products as the detrimental impurity which is very hardly to be eliminated through simple procedures of purification. This seems largely due to that a slight quantity of the rare earth metal chloride is soluble in organic solvents such as aromatic hydrocarbons, e.g., benzene, toluene and xylene.

In these circumstances, we, the inventors, have made extensive researches on the process of producing the rare earth metal alkoxide in an attempt to provide a new improved process which can be free from the aforesaid disadvantages of the prior art processes. As a result, we have now found that when an anhydrous rare earth metal carboxylate is employed as the starting material in place of the anhydrous rare earth metal chloride which had been employed in the prior art processes and when this anhydrous rare earth metal carboxylate is reacted with an alkali metal alkoxide, there can be produced the rare earth metal alkoxide of a higher purity in a higher yield than by the prior art processes and the rare earth metal alkoxide as produced can easily be recovered. On the basis of these findings, we have finished this invention.

DETAILED DESCRIPTION OF THE INVENTION

According to this invention, therefore, there is provided a process for the production of a rare earth metal alkoxide represented by the general formula $$M(OR)_3 \qquad (I)$$

wherein M denotes a rare earth metal element and R denotes an alkyl group, which comprises reacting a rare earth metal carboxylate represented by the general formula $$M_nX_3 \quad (II)$$

wherein M is as defined above, X denotes the residue of a carboxylic acid and n is an integer of 1 or 2, provided that n is 1 when X denotes the residue of a mono-carboxylic acid; and n is 2 when X denotes the residue of a di-carboxylic acid, with an alkali metal alkoxide represented by the general formula $$ROM' \quad (III)$$

wherein R is an alkyl group as defined above and M' denotes an alkali metal, in an inert organic solvent or liquid as the reaction medium under the anhydrous conditions.

To depict the differences between the process of this invention and the aforesaid prior art processes, the reactions involved in these processes are shown briefly by the following reaction equations in comparison.

(1) According to the process of this invention:

$$M_nX_3 \;+\; 3n\;ROM' \longrightarrow n\;M(OR)_3$$

| Anhydrous rare earth metal carboxylate | Alkali metal alkoxide | Rare earth metal alkoxide | where M, M', X, R and n have the same meanings as defined above.

(2) According to the prior art processes:
(i) The first process:-

$$ScCl_3 \;+\; 3\;CH_3OH \longrightarrow Sc(OCH_3)_3$$

| Scandium chloride | Methanol | Scandium methoxide |

[namely, the process described in the above-mentioned "Z. Anorg. Allgem. Chem."].

(ii) The second process:-

(a) $M''Cl_3 \;+\; 3\;CH_3OLi \longrightarrow M''(OCH_3)_3$

| Anhydrous rare earth- metal chloride | Lithium methoxide | Rare earth metal alkoxide | where M'' denotes Pr, Nd or La.
[namely, the process described in the above-mentioned "Proc. Nucl. Radiation Chem. Symp."].

(b) $M''Cl_3 \;+\; 3\;n\text{-}C_4H_9ONa \longrightarrow M''(O\text{—}n\text{-}C_4H_9)_3$

| Anhydrous rare earth metal chloride | Sodium n-butoxide | Rare earth metal n-butoxide | where M'' has the same meaning as defined just above.
[namely, the process described in the aforesaid "Chem. and Industry".].

(c) $SmCl_3 \;+\; 3\;R'ONa \longrightarrow Sm(OR')_3$

| Anhydrous samarium chloride | Sodium alkoxide | Samarium alkoxide | where R' denotes methyl, isopropyl, n-butyl, sec-butyl, tert-butyl or n-amyl group.
[Ditto].

(d) $M'''Cl_3 \;+\; 3\;R''ONa \longrightarrow M'''(OR'')_3$

| Anhydrous rare earth metal chloride | Sodium alkoxide | Rare earth metal alkoxide | where M''' stands for Gd, Er or Yb and R'' stands for methyl, ethyl, n-propyl, n-butyl, iso-amyl or tert-amyl group.
[Ditto].

(e) $YCl_3 \;+\; 3\;CH_3ONa \longrightarrow Y(OCH_3)_3$

| Anhydrous yttrium chloride | Sodium methoxide | Yttrium methoxide |

[namely, the process described in the aforesaid "Chem. Ber."].

(f) $YCl_3 \;+\; 3\;R'''OLi \longrightarrow Y(OR''')_3$

| Anhydrous yttrium chloride | Lithium alkoxide | Yttrium alkoxide | where R''' denotes isopropyl, tert-butyl, sec-pentyl, sec-hexyl or tert-heptyl group.
[namely, the process described in U.S. Pat. No. 3,278,571].
(iii) The third process:-

$$Y \;+\; 3\;i\text{-}C_3H_7OH \xrightarrow{HgCl_2(catalyst)} 3\;Y(O\text{—}i\text{-}C_3H_7)_3$$

| Yttrium, metallic | Isopropanol | Yttrium isopropoxide |

[namely, the process described in the aforesaid "Inorg. Chem." and the U.S. Pat. No. 3,278,571 specification].

According to the process of this invention, it is feasible to produce a rare earth metal alkoxide of a high purity in a favorably high yield. The rare earth metal alkoxide of a high purity can be obtained at a low cost without requiring special purification of the rare earth metal alkoxide. Thus, the process of this invention can afford in a yield of 90% or more such a rare earth metal alkoxide product which is substantially not containing the detrimental impurities therein. Accordingly, it is clear that the process of this invention can provide remarkable improvements in respect of the yield of and purity of the aimed product as well as the simplicity and cost of the process to be operated, as compared to the aforesaid prior art processes by which only the rare earth metal alkoxide containing considerable quantities of the impurities is afforded in a poor yield.

The process for the production of a rare earth metal alkoxide according to this invention is now described in more details. This process can be carried out in a facile way merely by adding a stoichiometrial or substantially stoichiometrial quantity of an alkali metal alkoxide of the general formula (III) to a solution or suspension of a rare earth metal carboxylate of the general formula (II) in an inert organic solvent or liquid and then stirring the resultant admixture for a time of 1–3 hours at such a temperature which may range from ambient temperature to the refluxing temperature of the solvent employed. The reaction of the alkali metal alkoxide with the rare earth metal carboxylate is necessary to be conducted under the anhydrous conditions, since the hydrolysis of the resulting rare earth metal alkoxide as produced can take place if there is present a significant amount of water in the reaction system. After the reaction is complete, the reaction mixture is filtered to remove the alkali metal carboxylate which is insoluble in and deposited from the reaction medium, and in this way there is afforded as the filtrate a clear and homogenous solution of the desired rare earth metal alkoxide in the organic solvent. It is preferred that the filtrate should be concentrated to dryness by evaporation of the solvent and the residue then may be admixed with a volume of an aromatic hydrocarbon such as benzene, toluene, xylene, for re-dissolution of the rare earth metal alkoxide. The solution so obtained may then be filtered again if there is remaining some insoluble matters comprising the starting rare earth metal carboxylate which remains unreacted and is substantially insoluble in the aromatic hydrocarbon, as well as the by-produced alkali metal carboxylate which is also insoluble in the aromatic hydrocarbons. Thus, a clear and homogeneous solution of the desired rare earth metal alkoxide is obtained.

The rare earth metal carboxylate (II) which is used as the starting material in the reaction may be the salt of a mono-carboxylic acid or di-carboxylic acid with the rare earth metal and is supplied in the anhydrous form to the reaction. When a hydrous rare earth metal carboxylate is dissolved in benzene, toluene, xylene and the resultant solution is distilled, the water content can conveniently be removed by azeotropic distillation, affording the anhydrous rare earth metal carboxylate. In general, the rare metal carboxylate (II) may either be such one of the formula

wherein M denotes a rare earth metal and $R_a$ denotes a hydrogen atom or an alkyl group of 1 to 10 carbon atoms, or an optionally substituted aryl group such as phenyl and tolyl, or may be such one of the formula

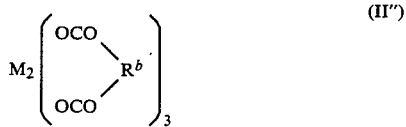

wherein M denotes a rare earth metal and $R_b$ denotes a chemical linkage bond or an alkylene group of 1-4 carbon atoms, such as methylene, and ethylene, or phenyl group. In the present process, it is preferred to use the formate, acetate, propionate, butyrate, oxalate, malonate, succinate or benzoate of the rare earth metal as the starting material. The rare earth metal formate, acetate, propionate, benzoate and oxalate are most preferred to be used as the starting material.

In the process of this invention, the rare earth metal carboxylate (II) may be reacted with the alkali metal alkoxide (III) in the stoichiometrical or substantially stoichiometrical proportions, and it is economically preferable to use 3 to 3.3 molar proportions of the alkali metal alkoxide and 0.85 to 5 liters of the organic solvent per 1 molar proportion of the anhydrous rare earth metal carboxylate. For the reaction medium in which the present process is carried out, any organic solvent or liquid in which the starting rare earth metal carboxylate and the alkali metal alkoxide reagent are soluble or dispersible may be used, as long as the organic solvent or liquid is inert to the reaction involved. Alkanols, preferably an alkanol of 1 to 10 carbon atoms, such as methanol, ethanol, hexanol, octanol and the like are preferred as the reaction medium in view of their high solvent-capacity and their easy handability. Such aromatic hydrocarbons as benzene, toluene, xylene and the like may be used as the reaction medium, as both the starting rare earth metal carboxylate and the alkali metal alkoxide reagent are hardly soluble but easily dispersible in these aromatic hydrocarbons. For a solvent for re-dissolution of the rare earth metal alkoxide product, it is possible to employ any inert organic solvent in which the rare earth metal alkoxide is soluble. In particular, such aromatic hydrocarbons as benzene, toluene, xylene and the like may preferably be employed for this re-dissolution purpose, because such an amount of the starting rare earth metal carboxylate which remains unreacted is not soluble in these aromatic hydrocarbons and thus is removable by filtration. When such aromatic hydrocarbon for the re-dissolution purpose is used in a volume of 0.5 to 5 l per 1 molar proportion of the starting anhydrous rare earth metal carboxylate, this volume of the aromatic hydrocarbon is sufficient to re-dissolve the rare earth metal alkoxide product as formed from the starting rare earth metal carboxylate material.

Normally, the rare earth metal alkoxide can readily undergo the hydrolysis even in the presence of a very slight amount of water, and owing to this, the rare earth metal alkoxide may preferably be provided to a subsequent application or processing, while being retained in the form of the solution in the dry organic solvent. If required, however, it is possible to isolate the rare earth metal alkoxide from the solution by distilling off the solvent and handling the solid residue carefully under the anhydrous conditions.

In accordance with the process of this invention, the procedure for reacting the rare earth metal carboxylate with the alkali metal alkoxide may comprise contacting the alkali metal alkoxide reagent immediately with the starting rare earth metal carboxylate dissolved or dispersed in an organic solvent or liquid, as shown briefly by the following equation:

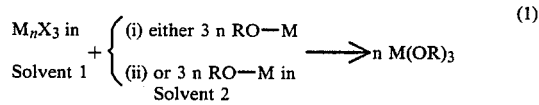

where M, M', R, X and n are as defined above.

Thus, in this embodiment of the process of the invention, the alkali metal alkoxide, either alone or as dissolved or suspended in Solvent 2 as an appropriate organic solvent or liquid, may be added to a solution or suspension of the anhydrous rare earth metal carboxylate dissolved or suspended in Solvent 1 as an appropriate organic solvent or liquid. Here, Solvent 1 and Solvent 2 may be the same or different and may independently be selected from the aromatic hydrocarbons such as benzene, toluene, xylene and the like, as well as the alkanols such as methanol, ethanol, butanol, octanol and the like. While, a further embodiment of the present process may comprise adding a metallic alkali metal to a solution of the anhydrous rare earth metal carboxylate in an alkanol solvent and thereby reacting the metallic alkali metal with the alkanol as the solvent, so as to form the necessary alkali metal alkoxide reagent in situ in the solution of the rare earth metal carboxylate, and then allowing the alkali metal alkoxide as formed, to be reacted in turn, with the rare earth metal carboxylate present in the solution. This further embodiment of the present process may briefly be represented by the following equation:

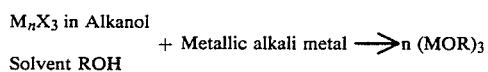  (2)

where M, R, X and n are as defined above.

Thus, in this further embodiment of the process, an alkali metal in the metallic state may be added to a solution of the starting anhydrous rare earth metal carboxylate in solution in an alkanol solvent of the formula ROH where R is as defined above. This alkanol solvent may either be selected from the alkanols such as methanol, ethanol, n-propanol, isopropanol, n-butanol, tert-butanol, octanol and the like and may be provided either alone or in mixture with an aromatic hydrocarbon such as benzene, toluene, xylene and the like. The metallic alkali metal so added can react with the solvent alkanol to produce the alkali metal alkoxide reagent in situ the solution of the starting rare earth metal carboxylate.

This invention is now illustrated with the following Examples to which this invention is limited in no way.

EXAMPLE 1

Production of yttrium methoxide (according to the first embodiment for the reaction)

Anhydrous yttrium acetate (8.0 g, 0.03 mol.) and benzene (50 ml) were placed in a round-bottomed flask of 100 ml-capacity, to which was then added dropwise a methanolic solution of sodium methoxide (containing 0.09 mol. of $CH_3ONa$ at a concentration of 28% by weight) under stirring. After the addition of the sodium methoxide, the reaction mixture in the flask was refluxed for 2 hours by heating with aid of a mantle heater. The reaction solution was then allowed to cool to ambient temperature and then filtered to remove the deposited crystals (comprising the unreacted yttrium acetate and the by-produced sodium acetate). The filtrate obtained was concentrated to dryness by evaporation of the solvent and the residue was taken up into 30 ml of benzene added thereto. The resultant solution in benzene was filtered to remove the insoluble solids comprising the unreacted yttrium acetate and the by-produced sodium acetate, and to give a clear and homogeneous solution of yttrium methoxide in benzene. This solution in benzene was concentrated to dryness by evaporation of the solvent to afford 5.3 g of yttrium methoxide as a white colored crystals. Yield 96.6% Elemental analysis: Calcd.: C 19.8%, H 5.0%, O 26.4%, Found: C 19.6%, H 5.1%, O 26.1%.

EXAMPLES 2–22

The process of Example 1 was repeated using such different rare earth metal carboxylates, such different alkali metal alkoxides, and such different organic solvents (or organic liquid) for the rare earth metal carboxylate as indicated in Table 1 below, and effecting the reaction according to the first embodiment (the first reaction procedure) of this invention. The alkali metal alkoxide employed was supplied as a solution of it in the alkanol from which the alkali metal alkoxide was derived.

TABLE 1

| Ex. | Rare earth metal Carboxylate [g], (mol.) | Solvent (ml) | Alkali metal alkoxide (mol.) | Reaction temp. (°C.) | Reaction time (hrs.) | Products [g] | Yield (%) | Calcd. C | Calcd. H | Calcd. O | Found C | Found H | Found O |
|---|---|---|---|---|---|---|---|---|---|---|---|---|---|
| 2 | scandium formate $Sc(OCOH)_3$ [5.4] (0.03) | toluene (50) | sodium methoxide (0.09) | solvent refluxing | 3 | $Sc(OCH_3)_3$ [3.8] | 91.6 | 26.1 | 6.5 | 34.8 | 25.4 | 6.8 | 33.9 |
| 3 | $Y(OCOH)_3$ [6.7] (0.03) | toluene (50) | sodium methoxide (0.09) | solvent refluxing | " | $Y(OCH_3)_3$ [5.0] | 90.8 | 19.8 | 4.9 | 26.4 | 20.1 | 5.1 | 25.8 |
| 4 | $Pr(OCOH)_3$ [8.3] (0.03) | toluene (50) | sodium methoxide (0.09) | solvent refluxing | " | $Pr(OCH_3)_3$ [6.6] | 93.5 | 15.4 | 3.8 | 20.5 | 15.6 | 3.7 | 20.2 |
| 5 | $Nd(OCOH)_3$ [8.4] (0.03) | toluene (50) | sodium methoxide (0.09) | solvent refluxing | " | $Nd(OCH_3)_3$ [6.9] | 90.5 | 15.2 | 3.8 | 20.2 | 15.6 | 3.8 | 20.9 |
| 6 | $Sm(OCOH)_3$ [8.6] (0.03) | toluene (50) | sodium methoxide (0.09) | solvent refluxing | " | $Sm(OCH_3)_3$ [6.4] | 94.2 | 14.8 | 3.7 | 19.7 | 15.2 | 3.6 | 20.9 |
| 7 | $Dy(OCOH)_3$ [8.9] (0.03) | toluene (50) | sodium methoxide (0.09) | solvent refluxing | " | $Dy(OCH_3)_3$ [7.2] | 94.0 | 14.1 | 3.5 | 18.8 | 15.1 | 3.2 | 18.8 |
| 8 | $Yb(OCOH)_3$ [9.2] (0.03) | toluene (50) | sodium methoxide (0.09) | solvent refluxing | " | $Yb(OCH_3)_3$ [7.3] | 91.9 | 13.5 | 3.4 | 18.0 | 13.5 | 3.7 | 18.8 |
| 9 | yttrium acetate $Y(OCOCH_3)_3$ [8.0] (0.03) | toluene (50) | lithium iso-propoxide (0.09) | solvent refluxing | 2 | $Y(O-i-C_3H_7)_3$ [7.7] | 97.1 | 40.7 | 8.0 | 18.1 | 40.5 | 8.2 | 18.1 |
| 10 | scandium oxalate | xylene (50) | potassium tert- | solvent re- | " | $Sc(O-t-C_7H_9)_3$ [7.3] | 92.3 | 54.5 | 10.2 | 18.2 | 56.1 | 10.4 | 17.7 |

TABLE 1-continued

| Ex. | Rare earth metal Carboxylate [g], (mol.) | Solvent (ml) | Alkali metal alkoxide (mol.) | Reaction temp. (°C.) | Reaction time (hrs.) | Products [g] | Yield (%) | Calcd. C | Calcd. H | Calcd. O | Found C | Found H | Found O |
|---|---|---|---|---|---|---|---|---|---|---|---|---|---|
|  | Sc$_2$(C$_2$O$_4$)$_3$ [5.3] (0.015) |  | butoxide (0.099) | fluxing |  |  |  |  |  |  |  |  |  |
| 11 | Y$_2$(C$_2$O$_4$)$_3$ [6.6] (0.015) | xylene (50) | potassium tert-butoxide (0.099) | solvent refluxing | " | Y(O—t-C$_4$H$_9$)$_3$ [8.4] | 90.8 | 46.8 | 8.8 | 15.6 | 46.1 | 8.3 | 16.6 |
| 12 | Dy(C$_2$O$_4$)$_3$ [8.8] (0.015) | xylene (50) | potassium tert-butoxide (0.099) | solvent refluxing | " | Dy(O—t-C$_4$H$_9$)$_3$ [10.4] | 91.1 | 37.7 | 7.1 | 12.6 | 38.2 | 7.5 | 12.4 |
| 13 | Yb$_2$(C$_2$O$_4$)$_3$ [9.2] (0.015) | xylene (50) | potassium tert-butoxide (0.099) | solvent refluxing | " | Yb(O—t-C$_4$H$_9$)$_3$ [10.7] | 91.8 | 36.7 | 6.9 | 12.2 | 35.8 | 7.1 | 11.9 |
| 14 | Y(OCOH)$_3$ [6.7] (0.03) | benzene (50) | sodium n-hexyrate (0.099) | solvent refluxing | 3 | Y(O—n-C$_6$H$_{13}$)$_3$ [10.7] | 92.4 | 55.1 | 10.0 | 12.2 | 57.1 | 10.6 | 11.8 |
| 15 | Sm(OCOH)$_3$ [8.6] (0.03) | benzene (50) | sodium n-hexyrate (0.099) | solvent refluxing | " | Sm(O—n-C$_6$H$_{13}$)$_3$ [12.4] | 91.1 | 47.7 | 8.6 | 10.6 | 47.1 | 8.2 | 11.3 |
| 16 | Dy(OCOH)$_3$ [8.9] (0.03) | benzene (50) | sodium n-hexyrate (0.099) | solvent refluxing | " | Dy(O—n-C$_{C_6H_{13}}$)$_3$ [12.7] | 90.5 | 46.4 | 8.5 | 10.3 | 45.3 | 8.8 | 10.9 |
| 17 | Yb(OCOH)$_3$ [9.2] (0.03) | benzene (50) | sodium n-hexyrate (0.099) | solvent refluxing | " | Yb(O—n-C$_6$H$_{13}$)$_3$ [13.0] | 91.1 | 45.4 | 8.2 | 10.1 | 45.1 | 8.1 | 11.1 |
| 18 | Y(OCOCH$_3$)$_3$ [8.0] (0.03) | benzene (50) | sodium 3-heptyrate (0.099) | solvent refluxing | 1 | Y[O—CH(C$_2$H$_5$)-n-C$_4$H$_9$]$_3$ [12.6] | 95.8 | 58.1 | 10.4 | 11.1 | 59.2 | 10.1 | 11.0 |
| 19 | yttrium benzoate Y(OCO—⬡)$_3$ | xylene (50) | lithium n-propoxide (0.099) | solvent refluxing | 2 | Y(O—n-C$_3$H$_7$)$_3$ [7.2] | 90.8 | 40.6 | 7.9 | 18.1 | 40.3 | 8.1 | 17.6 |
| 20 | Gd(OCO—⬡)$_3$ [13.71] (0.03) | xylene (50) | lithium n-propoxide (0.099) | solvent refluxing | " | Gd(O—n-C$_3$H$_7$)$_3$ [9.2] | 92.4 | 32.3 | 6.3 | 14.4 | 32.6 | 6.3 | 14.1 |
| 21 | Dy(OCO—⬡)$_3$ [13.8] (0.03) | xylene (50) | lithium n-propoxide (0.099) | solvent refluxing | " | Dy(O—n-C$_3$H$_7$)$_3$ [9.2] | 90.6 | 31.8 | 6.2 | 14.1 | 30.9 | 6.4 | 14.0 |
| 22 | Yb(OCO—⬡)$_3$ [14.2] (0.03) | xylene (50) | lithium n-propoxide (0.099) | solvent refluxing | " | Yb(O—n-C$_3$H$_7$)$_3$ [9.6] | 91.3 | 30.9 | 6.0 | 13.7 | 30.7 | 6.1 | 14.1 |

EXAMPLE 23

Production of scandium ethoxide (according to the second embodiment of the process)

Scandium propionate (0.03 mol.), benzene (50 ml) and ethanol (10 ml) were placed in a round-bottomed flask of 100 ml-capacity, to which was then added slowly 0.6 g (0.09 mol.) of metallic lithium under stirring. After the addition of the metallic lithium, the admixture in the flask was refluxed for 1 hour by heating with aid of a mantle heater, and then the reaction solution was processed in the same manner as in Example 1 to afford 6.4 g of scandium ethoxide as a white colored crystal. Yield 95.6%

Elemental analysis: Calcd.: C 32.2%, H 6.7%, O 21.4%, Found: C 31.8%, H 6.7%, O 21.1%.

EXAMPLES 24–55

The process of Example 23 was repeated using such different rare earth metal carboxylates, such different metallic alkali metals and such different alkanol solvents as indicated in Table 2 below, and effecting the reaction according to the second embodiment (the second reaction procedure) of this invention.

TABLE 2

| Ex. | Rare earth-metal Carboxylate [g], (mol.) | Solvent (ml) | Alkanol (ml) | Alkali metal (mol.) | Reaction temp. (°C.) | Reaction time (hrs.) | Products [g] | Yield (%) | Elemental analysis (%) Calcd. | | | Found | | |
|---|---|---|---|---|---|---|---|---|---|---|---|---|---|---|
| | | | | | | | | | C | H | O | C | H | O |
| 24 | lanthanium propionate La(OCOC$_2$H$_5$)$_3$ [11.2] (0.03) | benzene (50) | ethanol (10) | lithium (0.09) | solvent re-fluxing | 1 | La(OC$_2$H$_5$)$_3$ [7.5] | 91.6 | 26.3 | 5.5 | 17.5 | 26.2 | 5.3 | 18.2 |
| 25 | Ce(OCOC$_2$H$_5$)$_3$ [12.8] (0.03) | benzene (50) | ethanol (10) | lithium (0.09) | solvent re-fluxing | " | Ce(OC$_2$H$_5$)$_3$ [7.7] | 93.3 | 26.2 | 5.5 | 17.5 | 26.0 | 5.3 | 17.7 |
| 26 | Eu(OCOC$_2$H$_5$)$_3$ [13.1] (0.03) | benzene (50) | ethanol (10) | lithium (0.09) | solvent re-fluxing | " | Eu(OC$_2$H$_5$)$_3$ [7.8] | 90.6 | 25.1 | 5.2 | 16.7 | 24.4 | 5.0 | 17.0 |
| 27 | Gd(OCOC$_2$H$_5$)$_3$ [13.3] (0.03) | benzene (50) | ethanol (10) | lithium (0.09) | solvent re-fluxing | " | Gd(OC$_2$H$_5$)$_3$ [8.1] | 92.2 | 24.6 | 5.1 | 16.4 | 24.1 | 5.3 | 16.0 |
| 28 | Tb(OCOC$_2$H$_5$)$_3$ [13.3] (0.03) | benzene (50) | ethanol (10) | lithium (0.09) | solvent re-fluxing | " | Tb(OC$_2$H$_5$)$_3$ [8.3] | 93.7 | 24.5 | 5.1 | 16.3 | 24.7 | 5.5 | 17.0 |
| 29 | Dy(OCOC$_2$H$_5$)$_3$ [13.4] (0.03) | benzene (50) | ethanol (10) | lithium (0.09) | solvent re-fluxing | " | Dy(OC$_2$H$_5$)$_3$ [8.4] | 94.3 | 24.2 | 5.0 | 16.1 | 24.7 | 5.1 | 16.0 |
| 30 | Ho(OCOC$_2$H$_5$)$_3$ [13.5] (0.03) | benzene (50) | ethanol (10) | lithium (0.09) | solvent re-fluxing | " | Ho(OC$_2$H$_5$)$_3$ [8.1] | 90.1 | 24.0 | 5.0 | 16.0 | 24.0 | 4.8 | 16.6 |
| 31 | Er(OCOC$_2$H$_5$)$_3$ [13.6] (0.03) | benzene (50) | ethanol (10) | lithium (0.09) | solvent re-fluxing | " | Er(OC$_2$H$_5$)$_3$ [8.6] | 95.3 | 23.8 | 5.0 | 15.9 | 23.3 | 4.9 | 16.1 |
| 32 | Tm(OCOC$_2$H$_5$)$_3$ [13.6] (0.03) | benzene (50) | ethanol (10) | lithium (0.09) | solvent re-fluxing | " | Tm(OC$_2$H$_5$)$_3$ [8.4] | 91.9 | 23.7 | 4.9 | 15.8 | 24.0 | 5.1 | 16.3 |
| 33 | Yb(OCOC$_2$H$_5$)$_3$ [13.7] (0.03) | benzene (50) | ethanol (10) | lithium (0.09) | solvent re-fluxing | " | Yb(OC$_2$H$_5$)$_3$ [8.9] | 96.0 | 23.4 | 4.9 | 15.6 | 24.4 | 5.0 | 16.1 |
| 34 | Lu(OCOC$_2$H$_5$)$_3$ [13.8] (0.03) | benzene (50) | ethanol (10) | lithium (0.09) | solvent re-fluxing | " | Lu(OC$_2$H$_5$)$_3$ [8.5] | 91.1 | 23.2 | 4.8 | 15.5 | 24.0 | 5.0 | 15.5 |
| 35 | scandium acetate Sc(OCOCH$_3$)$_3$ [6.7] (0.03) | toluene (50) | isopropyl alcohol (10) | sodium (0.09) | 80 | 2 | Sc(O—i-C$_3$H$_7$)$_3$ [6.1] | 92.3 | 48.6 | 9.5 | 21.6 | 47.1 | 9.9 | 20.9 |
| 36 | La(OCOCH$_3$)$_3$ [9.5] | toluene (50) | isopropyl alcohol (10) | sodium (0.09) | " | " | La(O—i-C$_3$H$_7$)$_3$ [9.0] | 94.6 | 34.2 | 6.6 | 15.2 | 34.0 | 6.7 | 14.8 |
| 37 | Ce(OCOCH$_3$)$_3$ [9.5] | toluene (50) | ispropyl alcohol (10) | sodium (0.09) | " | " | Ce(O—i-C$_3$H$_7$)$_3$ [8.6] | 90.6 | 34.1 | 6.6 | 15.1 | 33.4 | 6.7 | 15.4 |
| 38 | Pr(OCOCH$_3$)$_3$ [9.5] | toleune (50) | isopropyl alocohol (10) | sodium (0.9) | " | " | Pr(O—i-C$_3$H$_7$)$_3$ [9.0] | 93.9 | 34.0 | 6.6 | 15.1 | 34.4 | 6.9 | 16.0 |
| 39 | Nd(OCOCH$_3$)$_3$ [9.6] | toluene (50) | isopropyl alcohol (10) | sodium (90) | " | " | Nd(O—i-C$_3$H$_7$)$_3$ [8.8] | 91.0 | 33.6 | 6.5 | 14.9 | 34.0 | 6.6 | 15.2 |
| 40 | Sm(OCOCH$_3$)$_3$ [9.8] | toluene (50) | isopropyl alcohol (10) | sodium (90) | " | " | Sm(O—i-C$_3$H$_7$)$_3$ [9.4] | 95.2 | 33.0 | 6.4 | 14.7 | 34.1 | 6.7 | 15.0 |
| 41 | EU(OCOCH$_3$)$_3$ [9.9] | toluene (50) | Isopropyl alcohol (10) | Sodium (90) | " | " | EU(O—i-C$_3$H$_7$)$_3$ [8.8] | 90.0 | 32.8 | 6.4 | 14.6 | 32.1 | 6.6 | 15.1 |
| 42 | GD(OCOCH$_3$)$_3$ [10.0] | toluene (50) | isopropyl alcohol (10) | Sodium (90) | " | " | Gd(O—i-C$_3$H$_7$)$_3$ [9.4] | 94.4 | 32.3 | 6.3 | 14.4 | 32.0 | 6.0 | 14.8 |
| 43 | Td(OCOCH$_3$)$_3$ [10.1] | toluene (50) | isopropyl alcohol (10) | sodium (90) | " | " | Td(O—i-C$_3$H$_7$)$_3$ [9.3] | 91.8 | 32.2 | 6.3 | 14.3 | 32.1 | 6.4 | 14.6 |
| 44 | Dy(OCOCH$_3$)$_3$ [10.2] | toluene (50) | isopropyl alcohol (10) | sodium (90) | " | " | Dy(O—i-C$_3$H$_7$)$_3$ [9.6] | 94.4 | 31.8 | 6.2 | 14.1 | 31.1 | 6.2 | 14.8 |
| 45 | Ho(OCOCH$_3$)$_3$ | toluene | isopropyl | sodium | " | " | Ho(O—i-C$_3$H$_7$)$_3$ | 92.3 | 31.6 | 6.1 | 14.0 | 32.2 | 6.6 | 14.4 |

TABLE 2-continued

| Ex. | Rare earth-metal Carboxylate [g], (mol.) | Solvent (ml) | Alkanol (ml) | Alkali metal (mol.) | Reaction temp. (°C.) | Reaction time (hrs.) | Products [g] | Yield (%) | Elemental analysis (%) Calcd. C | H | O | Found C | H | O |
|---|---|---|---|---|---|---|---|---|---|---|---|---|---|---|
| | [10.3] | (50) | alcohol (10) | (90) | | | [9.5] | | | | | | | |
| 46 | Er(OCOCH₃)₃ [10.3] | toluene (50) | isopropyl alcohol (10) | sodium (0.09) | " | " | Er(O—i-C₃H₇)₃ [9.8] | 94.7 | 31.4 | 6.1 | 13.9 | 31.0 | 6.3 | 14.2 |
| 47 | Tm(OCOCH₃)₃ [10.4] | toluene (50) | isopropyl alcohol (10) | sodium (0.09) | " | " | Tm(O—i-C₃H₇)₃ [9.5] | 91.2 | 31.2 | 6.1 | 13.9 | 32.0 | 6.3 | 14.0 |
| 48 | Yb(OCOCH₃)₃ [10.5] | toluene (50) | isopropyl alcohol (10) | sodium (0.09) | " | " | Yb(O—i-C₃H₇)₃ [9.9] | 94.8 | 30.9 | 6.0 | 13.7 | 30.1 | 6.0 | 13.9 |
| 49 | Lu(OCOCH₃)₃ [10.6] | toluene (50) | isopropyl alcohol (10) | sodium (0.09) | " | " | Lu(O—i-C₃H₇)₃ [9.7] | 92.0 | 30.7 | 6.0 | 13.6 | 30.2 | 6.4 | 14.2 |
| 50 | Y(OCOCH₃)₃ [8.0] | none | n-octyl alcohol (70) | lithium (0.09) | " | " | Y(O—n-C₈H₁₇)₃ [13.6] | 95.3 | 60.5 | 10.7 | 10.1 | 61.4 | 10.9 | 10.0 |
| 51 | Sm(OCOCH₃)₃ [9.8] | " | n-octyl alcohol (70) | lithium (0.09) | solvent refluxing | " | Sm(O—n-C₈H₁₇)₃ [14.7] | 91.1 | 53.6 | 9.5 | 8.9 | 54.2 | 10.0 | 8.8 |
| 52 | Dy(OCOCH₃)₃ [10.2] | " | n-octyl alcohol (70) | lithium (0.09) | solvent refluxing | 3 | Dy(O—n-C₈H₁₇)₃ [15.0] | 91.1 | 52.4 | 9.3 | 8.7 | 52.6 | 9.8 | 8.4 |
| 53 | Yb(OCOCH₃)₃ [10.5] | " | n-octyl alcohol (70) | lithium (0.09) | solvent refluxing | " | Yb(O—n-C₈H₁₇)₃ [15.3] | 91.3 | 51.4 | 9.1 | 8.6 | 51.1 | 9.0 | 8.8 |
| 54 | Y(OCOCH₃)₃ [8.0] | benzene (50) | ethanol (10) | potas-(sium) (0.9) | solvent refluxing | 1 | Y(O—C₂H₅)₃ [6.6] | 97.5 | 32.2 | 6.7 | 21.4 | 32.5 | 6.8 | 21.1 |
| 55 | Y(OCOCH₃)₃ [8.0] | xylene (60) | tert-butanol (10) | sodium (0.09) | 80 | 1.5 | Y(O—t-C₄H₉)₃ [8.9] | 96.0 | 46.8 | 8.9 | 15.6 | 46.4 | 8.8 | 15.4 |

COMPARATIVE EXAMPLE 1

(according to the prior art process described in the aforesaid "Inorg. Chem." Vol. 5(3).)

Lithium isopropoxide (24.3 g, 0.37 mol.) and isopropyl alcohol (150 ml) were placed in a round-bottomed flask of a 300 ml-capacity, to which was then added dropwise a solution of anhydrous yttrium trichloride (23.4 g, 0.12 mol.) in 25 ml of tetrahydrofuran under stirring. After the addition of the yttrium trichloride, the mixture in the flask was stirred at 45° C. for 3 hours with heating by means of a mantle heater, followed by concentration of the reaction solution to dryness by evaporation of the solvent. The residue obtained was admixed with 150 ml of benzene and the resultant solution was filtered to remove the insoluble matter. Distillation off of the benzene from the filtered solution gave 16.8 g of yttrium isopropoxide as a slightly yellow crystal. Yield 52.6%

COMPARATIVE EXAMPLES 2-16

The process of Comparative Example 1 was repeated using such different anhydrous rare earth metal trichlorides and such different alkali metal alkoxides as indicated in Table 3 below. The test results obtained are tabulated in Table 3.

TABLE 3

| Comparative Ex. | Rare earth metal chloride (mol.) | Alkali metal alkoxide (mol.) | Reaction time (heating & stirring) (hrs.) | Products (g) | Yield (%) |
|---|---|---|---|---|---|
| 2 | ScCl₃ (18.2) [0.12] | NaOCH₃ (0.37) | 3 | Sc(OCH₃)₃ (7.0) | 42.3 |
| 3 | LaCl₃ (29.4) [0.12] | NaO—i-C₃H₇ (0.37) | " | La(O—i-C₃H₇)₃ (17.3) | 50.3 |
| 4 | CeCl₃ (29.6) [0.12] | KOC₂H₅ (0.37) | " | Ce(OC₂H₅)₃ (18.6) | 56.4 |
| 5 | PrCl₃ (29.7) [0.12] | KO—i-C₃H₅ (0.37) | " | Pr(O—i-C₃H₇)₃ (14.0) | 40.5 |
| 6 | NdCl₃ (30.1) [0.12] | LiO—i-C₃H₇ (0.37) | 2 | Nd(O—i-C₃H₇)₃ (17.1) | 48.9 |
| 7 | SmCl₃ | LiO—n-C₈H₁₇ | " | Sm(O—n-C₈H₁₇)₃ | 33.1 |

TABLE 3-continued

| Comparative Ex. | Rare earth metal chloride (mol.) | Alkali metal alkoxide (mol.) | Reaction time (heating & stirring) (hrs.) | Products (g) | Yield (%) |
|---|---|---|---|---|---|
| 8 | EuCl$_3$ (31.0) [0.12] | NaO—n-C$_6$H$_{13}$ (0.37) | " | Eu(O—n-C$_6$H$_{13}$)$_3$ (22.4) | 41.0 |
| 9 | GdCl$_3$ (31.6) [0.12] | NaO—i-C$_3$H$_7$ (0.37) | 3 | Gd(O—i-C$_3$H$_7$)$_3$ (20.6) | 56.4 |
| 10 | TbCl$_3$ (31.8) [0.12] | KO—t-C$_4$H$_9$ (0.37) | 2 | Tb(O—t-C$_4$H$_9$)$_3$ (17.9) | 39.4 |
| 11 | DyCl$_3$ (32.3) [0.12] | KO—n-C$_3$H$_7$ (0.37) | " | Dy(O—n-C$_3$H$_7$)$_3$ (18.3) | 49.2 |
| 12 | HoCl$_3$ (32.6) [0.12] | LiO—n-C$_4$H$_9$ (0.37) | 3 | Ho(O—n-C$_4$H$_9$)$_3$ (26.3) | 57.1 |
| 13 | ErCl$_3$ (32.8) [0.12] | LiO—i-C$_3$H$_7$ (0.37) | 3 | Er(O—i-C$_3$H$_7$)$_3$ (19.0) | 50.5 |
| 14 | TmCl$_3$ (33.0) [0.12] | KO—n-C$_4$H$_9$ (0.37) | 2 | Tm(O—n-C$_4$H$_9$)$_3$ (22.3) | 47.9 |
| 15 | YbCl$_3$ (33.5) [0.12] | KO—n-C$_3$H$_7$ (0.37) | 3 | Yb(O—i-C$_3$H$_7$)$_3$ (19.9) | 51.8 |
| 16 | LuCl$_3$ (33.8) [0.12] | NaOC$_2$H$_5$ (0.37) | " | Lu(OC$_2$H$_5$)$_3$ (20.5) | 55.1 |

COMPARATIVE EXAMPLE 17

(according to the prior art process described in the aforesaid "Zeit. Anorg. All. Chemie" pp. 67–71, 325(12) (1963))

Methanol (150 ml) and anhydrous scandium trichloride (ScCl$_3$, 6.1 g, 0.04 mol.) were placed in a round-bottomed flask of a 300 ml-capacity and subsequently heated under refluxing for 3 hours. After the reaction was completed, a stream of dry ammonia gas (0.12 mol.) was passed into the reaction solution in said flask, followed by heating for 1 hour under refluxing. The reaction solution was then filtered to remove the deposited, bulky crystals (comprising the scandium methoxide as formed). The crystalline product so collected was washed well with hot methanol to remove the by-formed ammonium chloride therefrom, affording 3.1 g of scandium methoxide as slightly yellow colored crystals.

Yield 56.3%.

What we claim is:

1. A process for the production of a rare earth metal alkoxide of the general formula

M(OR)$_3$     (I)

wherein M denotes a rare earth metal atom and R denotes an alkyl group, which comprises reacting a rare earth metal carboxylate represented by the general formula M$_n$X$_3$     (II)

wherein M is as defined above, X denotes the residue of a carboxylic acid and n is an integer of 1 or 2, provided that n is 1 when X denotes the residue of a mono-carboxylic acid; and n is 2 when X denotes the residue of a di-carboxylic acid, with an alkali metal alkoxide represented by the general formula

ROM'     (III)

wherein R is an alkyl group as defined above and M' denotes an alkali metal, in an inert organic solvent or liquid under the anhydrous conditions.

2. A process as claimed in claim 1 in which the rare earth metal carboxylate used is of the formula M(OCOR$^a$)$_3$ 3. A process as claimed in claim 1 in which the rare earth metal carboxylate used is of the formula

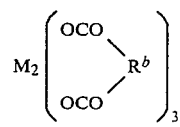

wherein M denotes a rare earth metal and R$^b$ denotes a chemical linkage bond or an alkylene group of 1–4 carbon atoms or phenyl group.

4. A process as claimed in claim 1 in which the rare earth metal carboxylate used is selected from the formate, acetate, propionate, benzoate and oxalate of the rare earth metal.

5. A process as claimed in claim 1 in which the inert organic solvent used as the reaction medium is selected from alkanols of 1 to 10 carbon atoms.

6. A process as claimed in claim 1 in which the inert organic solvent as the reaction medium is selected from benzene, toluene and xylene as aromatic hydrocarbons.

7. A process as claimed in claim 1 in which the inert organic solvent as the reaction medium is a mixture of benzene, toluene or xylene with an alkanol of 1 to 10 carbon atoms.

8. A process as claimed in claim 1 in which the reaction is conducted for a time of 1 to 3 hours at a temperature of ranging from ambient temperature to the refluxing temperature of the reaction medium.

9. A process as claimed in claim 1 in which the alkali metal alkoxide is such one that has been produced in situ in the solution of the rare earth metal carboxylate in an alkanol by reacting a metallic alkali metal with the solvent alkanol of said solution of the rare earth metal carboxylate.

10. A process as claimed in claim 1 in which the reaction mixture after completion of the reaction is concentrated to dryness, the solid residue is then re-dissolved in a volume of benzene, toluene or xylene, the solution so obtained is filtered to remove the insoluble solids therefrom and to afford a clear solution of the rare earth metal alkoxide in benzene, toluene or xylene.

* * * * *

UNITED STATES PATENT AND TRADEMARK OFFICE
CERTIFICATE OF CORRECTION

PATENT NO. : 4,507,245
DATED : March 26, 1985
INVENTOR(S) : OZAKI et al

It is certified that error appears in the above-identified patent and that said Letters Patent is hereby corrected as shown below:

On the cover page of the patent, lefthand column, under "foreign Application Data", change "57-1162468" to --57-116246--.

Signed and Sealed this

Twentieth Day of August 1985

[SEAL]

Attest:

DONALD J. QUIGG

Attesting Officer

Acting Commissioner of Patents and Trademarks